United States Patent
Dormann

(10) Patent No.: US 10,350,146 B2
(45) Date of Patent: Jul. 16, 2019

(54) PEG TUBE WITH A VALVE

(71) Applicant: KLINIKEN DER STADT KOELN GGMBH, Cologne (DE)

(72) Inventor: Arno Dormann, Cologne (DE)

(73) Assignee: KLINIKEN DER STADT KOELN GGMBH (DE)

( * ) Notice: Subject to any disclaimer, the term of this patent is extended or adjusted under 35 U.S.C. 154(b) by 197 days.

(21) Appl. No.: 15/521,234

(22) PCT Filed: Jul. 22, 2015

(86) PCT No.: PCT/EP2015/066781
§ 371 (c)(1),
(2) Date: Apr. 21, 2017

(87) PCT Pub. No.: WO2016/062418
PCT Pub. Date: Apr. 28, 2016

(65) Prior Publication Data
US 2017/0348197 A1  Dec. 7, 2017

(30) Foreign Application Priority Data
Oct. 21, 2014  (DE) ........................ 10 2014 115 340

(51) Int. Cl.
*A61J 15/00* (2006.01)
*A61M 39/22* (2006.01)
(Continued)

(52) U.S. Cl.
CPC ....... *A61J 15/0092* (2013.01); *A61J 15/0015* (2013.01); *A61J 15/0034* (2013.01);
(Continued)

(58) Field of Classification Search
CPC .. A61J 15/0015; A61J 15/0026; A61J 15/003; A61J 15/0034; A61J 15/0053;
(Continued)

(56) References Cited

U.S. PATENT DOCUMENTS 4,666,433 A   5/1987 Parks
5,098,378 A   3/1992 Piontek et al.
(Continued)

FOREIGN PATENT DOCUMENTS

DE   10051593 A1   5/2002
DE   10154864 A1   5/2003
(Continued)

OTHER PUBLICATIONS

International Preliminary Report on Patentability for Application No. PCT/EP2015/066781 dated Oct. 20, 2016, 6 pages.
International Search Report for Application No. PCT/EP2015/066781 dated Oct. 13, 2015, 3 pages.

*Primary Examiner* — Bhisma Mehta
*Assistant Examiner* — James D Ponton
(74) *Attorney, Agent, or Firm* — McCarter & English, LLP

(57) ABSTRACT

The invention relates to a PEG probe having a PEG tube, an outer holding plate, through which the PEG tube is fed and in which the PEG tube is fastened, and a funnel adapter, which is associated with an outer end region of the PEG tube. A tightly closing valve is arranged either in the PEG tube between the outer holding plate and the outer end region or on the outer end region of the PEG tube. The valve blocks the flow through the PEG tube in a closed position and allows said flow at least in the full cross-section of the PEG tube in an open position. The valve has a valve body and a valve housing. The valve body is connected to and movable by means of a handle accessible from outside. The valve body is supported in the valve housing.

20 Claims, 2 Drawing Sheets

(51) Int. Cl.
*A61M 39/10* (2006.01)
*A61M 39/02* (2006.01)

(52) U.S. Cl.
CPC .......... *A61J 15/0061* (2013.01); *A61M 39/10* (2013.01); *A61M 39/22* (2013.01); *A61M 39/0247* (2013.01); *A61M 2039/1077* (2013.01); *A61M 2039/226* (2013.01)

(58) Field of Classification Search
CPC .... A61J 15/0061; A61M 39/22; A61M 39/26; A61M 39/1011; A61M 2039/1061; A61M 2039/226; F16K 35/14; Y10T 137/87973
USPC .................................. 251/149.9; 137/614.06
See application file for complete search history.

(56) References Cited

U.S. PATENT DOCUMENTS

| | | | |
|---|---|---|---|
| 5,403,290 | A | 4/1995 | Noble |
| 2006/0079850 | A1* | 4/2006 | Adams .................. A61M 25/02 604/284 |
| 2008/0033364 | A1 | 2/2008 | Kamen et al. |
| 2009/0318854 | A1 | 12/2009 | Bailey |

FOREIGN PATENT DOCUMENTS

| | | |
|---|---|---|
| EP | 2221084 A1 | 8/2010 |
| JP | 2003038655 A | 2/2003 |
| WO | 2006036843 A1 | 4/2006 |

\* cited by examiner

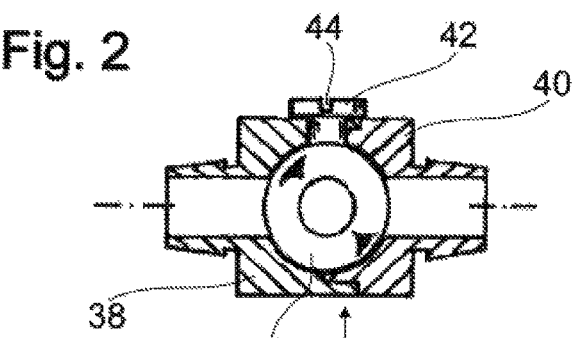
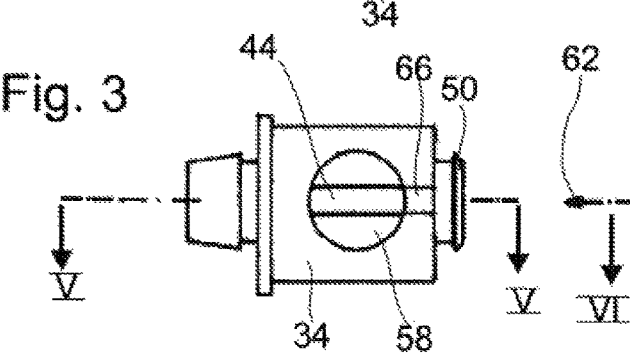
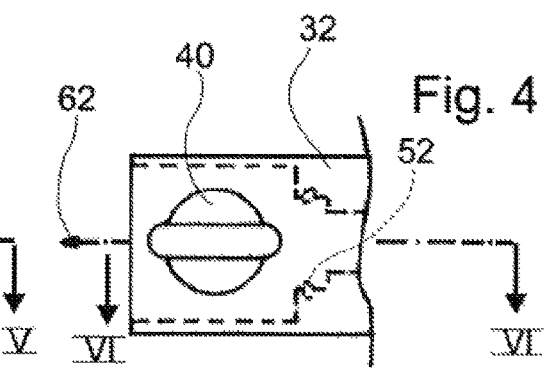
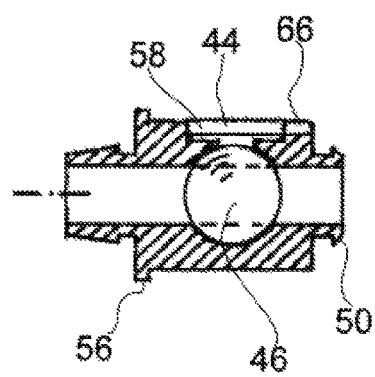
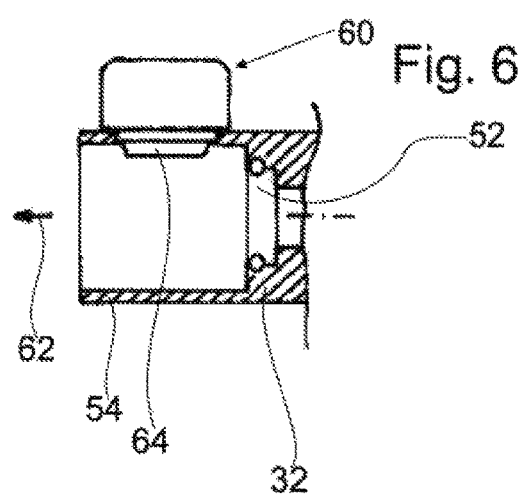
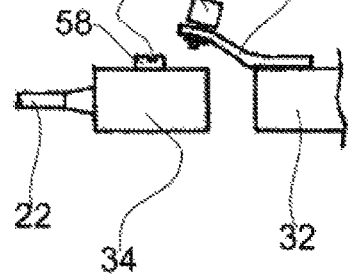

PEG TUBE WITH A VALVE

CROSS-REFERENCE TO RELATED APPLICATIONS

This application is a national stage application of international application no. PCT/EP2015/066781 filed Jul. 22, 2015, entitled "Peg Probe Having Protected Manual Valve Operation," claiming benefit under 35 U.S.C. §§ 119(a)-(d) to German application no. DE 10 2014 115 340.5 filed Oct. 21, 2014, which are hereby expressly incorporated by reference as part of the present disclosure.

FIELD OF INVENTION

The invention relates to a PEG tube
with an inner retaining plate,
with a PEG hose having an inner end portion and an outer end portion, the inner end portion being firmly connected to the inner retaining plate and having an inner opening of the PEG hose there,
with an outer retaining plate through which the PEG hose is routed,
with a funnel adapter associated with the outer end portion,
with a tightly sealing valve disposed at the outer end portion of the PEG hose, the valve blocking the flow-through through the PEG hose in a closing position and unblocking it in an opening position, the valve comprising a valve body and a valve housing, the valve body being connected to a handling means accessible from the outside and being mounted in the valve housing so as to be movable between the permanent closing position and the permanent opening position.

BACKGROUND

Such a PEG tube is known from WO 2006/036843 A1. Another tube is known from U.S. Pat. No. 4,666,433 A. PEG tubes, i.e. gastronomy feeding tubes offer access to the stomach at the location of a stoma. Such connections typically remain in position over extended periods of time and serve for feeding the patient and for administering medicaments. Several of the known PEG tubes have check valves that prevent the contents of the stomach from flowing back through the PEG hose and leaking from its outer opening; see, for example, US 2006/0079850 A1 and DE 101 54 864 A1. Thus, it is possible to prevent possibly acid stomach contents from leaking to the outside and causing damage there.

In the previously known PEG tube of the type mentioned in the introduction, the funnel adapter is firmly connected to the outer end portion of the PEG hose, and a sealing plug is provided with which the outer end of the funnel adapter can be sealed. Such sealing caps can be found frequently in PEG tubes. They seal the PEG hose; they prevent the entrance of foreign substances into the PEG hose from the outside. However, they do not offer a permanent seal.

Disengageable clamping seals are also known, which are generally also referred to as ratchet clamps and can be attached at any location of the PEG hose between the outer retaining plate and the outer end portion. Such a hose clamp is discussed in general terms in DE 100 51 593 A1. Such hose clamps are disadvantageous, however, in that they put great, excessive strain on the PEG hose in the long term and destroy it. When it is squeezed together it is put under excessive strain in the sharply bent corner areas of the hose that are formed at that time, and tends to form tears and, in the long term, to spring a leak.

SUMMARY

Based on this, it is the object of at least some embodiments of the invention to further develop the PEG tube of the type mentioned in the introduction in such a way that a secure seal of the PEG hose is obtained that can be opened and closed any number of times, can be permanently kept in a partially opened position, which is designed in such a way that it can be simply and directly operated only by means of accessories, and therefore not by a patient, and which provides the conditions for configuring the parts of the PEG tube located outside the body in such a way that they are as small and easy to carry as possible.

This object is achieved by a PEG tube
with an inner retaining plate,
with a PEG hose having an inner end portion and an outer end portion, the inner end portion being firmly connected to the inner retaining plate and having an inner opening of the PEG hose there,
with an outer retaining plate through which the PEG hose is routed and in which it is fixed,
with a funnel adapter associated with the outer end portion,
with a tightly sealing valve disposed at the outer end portion of the PEG hose, wherein the valve blocks the flow-through through the PEG hose in a closing position, partially unblocks it in an intermediate position, and unblocks it at least over the full cross section of the PEG hose in an opening position, wherein the valve comprises a valve body and a valve housing, the valve body is connected to a handling means accessible from the outside and is mounted in the valve housing so as to be movable between the permanent closing position and the permanent opening position, wherein the handling means has a multi-part configuration, a first part of the handling means is permanently disposed on the valve body and a second part of the handling means is disposed on the funnel adapter separately from the valve and, when the valve and the funnel adapter are plugged together, automatically engages the first part of the handling means, and the second part of the handling means comprises a tool cooperating with a matching tool counterpart of the first part, wherein the PEG hose is located only on an inner side of the valve, the valve is connected on the inner side to the end portion of the PEG hose and has at its other, outer side a coupling portion, the funnel adapter has a coupling counterpart matched to the coupling portion, and that the coupling portion and the coupling counterpart can be mechanically connected to and detached from each other in a tight manner.

The valve is disposed directly at the outer end portion of the PEG hose. This valve can be adjusted to any intermediate position between a closing position and an opening position. All end and intermediate positions can be set permanently. At least in the opening position, the valve has a free flow-through cross section that corresponds to that of the PEG hose or is greater. The valve has a handling means; the valve body is moved by the handling means; it can thus be moved back and forth between its two end positions. The movement can be a shifting movement along the longitudinal axis of the PEG hose, a rotary movement about the longitudinal axis of the PEG hose as an axis and a rotary movement transverse to the longitudinal axis and about an axis of the valve body. In the latter case, the advantage is realized that only a rotary movement is required to move the valve body. Thus, sealing from the inside towards the outside is simple.

The PEG hose is located only on one side of the valve; the funnel adapter is detachably connected to the valve. The funnel adapter is detachably placed and removed at the end of the valve facing away from the PEG hose. A coupling portion is provided on the valve; the funnel adapter has a coupling counterpart. The two coupling portions can be tightly connected to each other and then form a mechanically firm unit. In this way, the funnel adapter, which has an increasing volume over time due to various developments, and also due to a standardization that is to be expected, need not be constantly taken along. It can also be easily replaced with another model, with which medicaments can administered more easily, for example.

The valve can be cleaned well because its housing is manufactured from at least two sections. If they are separated from each other, the valve body is free and can thus be cleaned. This also applies to the parts of the valve body. In the assembled state of the two sections, they retain the valve body between them, preferably in an elastic manner.

The handling means has a multi-part configuration. In this case, a first part is permanently disposed on the valve body. Without using a tool, however, the valve body cannot be moved with this first part. Only the second part provides the required accessory or tool for being able to move the first part with the valve body located thereon. The second part is disposed on the funnel adapter in such a way that an operation of the valve body is only possible if the funnel adapter is placed on the valve. The connection between the funnel adapter and the valve is configured in such a way that the funnel adapter can only be detached from the valve if the valve is located in the closing position. It is thus ensured that the valve is closed when the funnel adapter is removed. A patient without an accessory is unable to simply open the valve without the funnel adapter.

When the valve and funnel adapter are plugged together, the second part of the handling means connected to the funnel adapter automatically engages the first part or is coupled with it in another manner, so that the first part can be operated by means of the second part. The second part comprises a tool; the first part has a matching tool counterpart. When the two are engaged, an operation of the valve body is manually possible with simple means. For this purpose, a grip of the second part is manually moved, for example rotated. Without the second part, the valve body can only be moved using special tools and not, in any case, with manual means, for example with the fingers of the patient.

Preferably, the tool located on the second part of the handling means is guided in a groove when the funnel adapter and the valve are plugged together. This makes a certain alignment of the funnel adapter and the valve relative to one another compulsory; the two can only be plugged together if the tool fits into the groove. When they are pushed together, the groove guides the tool in such a way that the tool engages or is coupled in another manner with the tool counterpart of the first part. A rib may also be provided instead of a groove. It is possible to configure the groove with an inclined portion so that the tool is lifted in the radial direction when the funnel adapter and the valve are joined. Thus, the tool is lifted and can click or latch into the counterpart tool once the final position has been reached.

In another embodiment, the second part of the handling means is flexibly connected to the funnel adapter, e.g. by a string or a flexible tab. The second part is available if the funnel adapter is in the vicinity, particularly if it is connected to the valve.

Preferably, the valve body is a geometrically simple item. Spherical valve bodies, conical or cylindrical valve bodies and disk-shaped valve bodies suggest themselves.

In any case, the valve is connected on one side to the PEG hose. Compression fittings as they are known from the prior art can be used for connecting the valve and the PEG hose, see, for example US 2006/0079850 A1, which, however, does not show a clamping union nut.

BRIEF DESCRIPTION OF DRAWINGS

Other advantages and features of the invention become apparent from the other claims as well as from the following description of exemplary embodiments of the invention, which are to be understood not to be limiting and which will be explained below in more detail with reference to the drawing. In the drawing:

FIG. 2 shows an axial sectional view through a valve with a two-part valve housing, FIG. 3 shows a top view of a valve that can be coupled to a funnel adapter, FIG. 4 shows a top view of a funnel adapter that matches the valve according to FIG. 3 and that can be connected with it, FIG. 5 shows a section through the valve according to FIG. 3 along the section line V-V, FIG. 6 shows a sectional view through the funnel adapter according to FIG. 4 along the section line VI-VI in FIG. 4, and FIG. 7 shows a schematic view of a valve and a funnel adapter that can be coupled to it; a tab on which a second part of the handling means is flexibly disposed is provided on the funnel adapter.

DETAILED DESCRIPTION OF EMBODIMENTS

Figure 1:
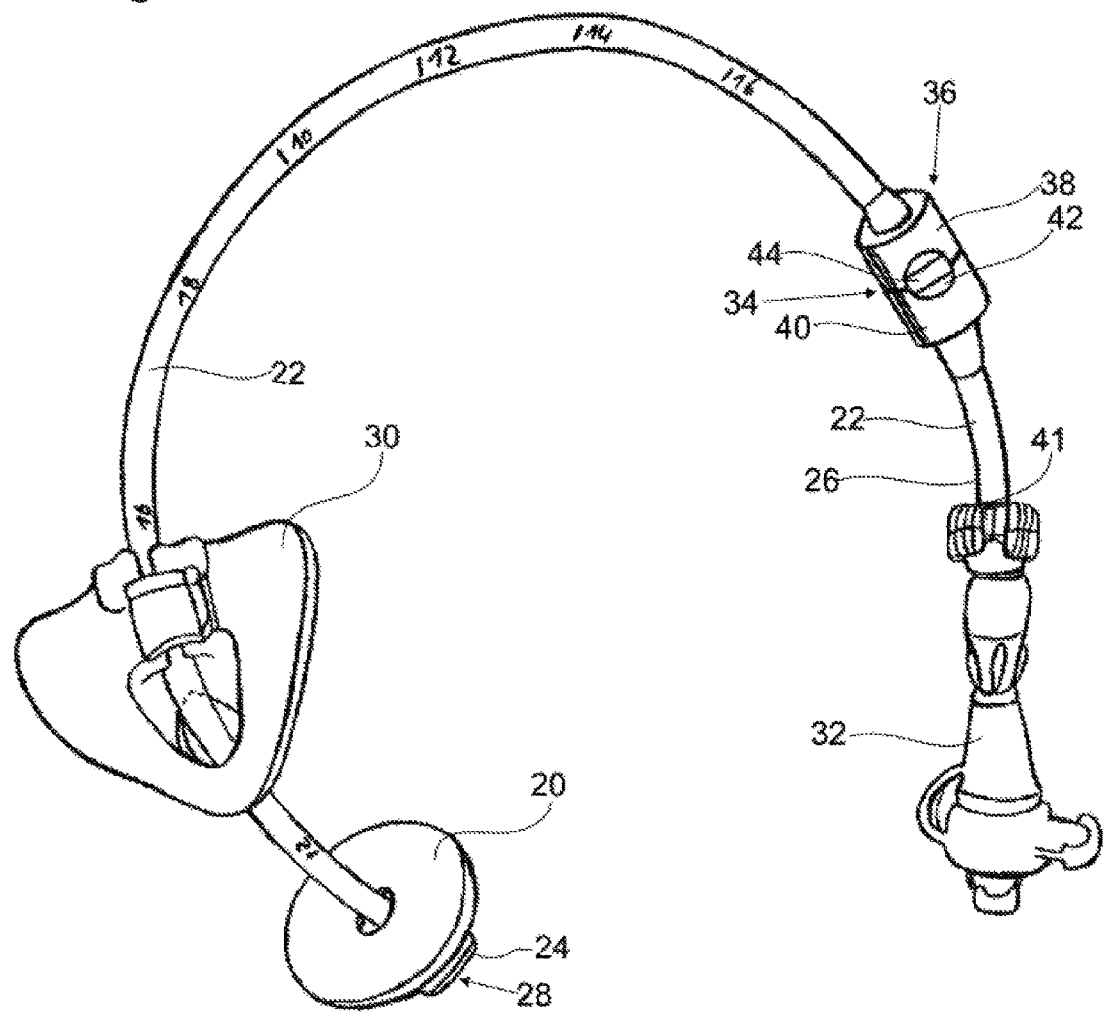
FIG. 1 shows a perspective illustration of a PEG tube according to a first exemplary embodiment.

FIG. 1 shows a first exemplary embodiment. FIG. 2 shows a second exemplary embodiment, FIGS. 3 to 6 show a third exemplary embodiment, and a fourth exemplary embodiment is shown in FIG. 7. Only the first exemplary embodiment shows an entire PEG tube; the other exemplary embodiments show parts thereof.

From FIG. 1, a PEG tube with an inner retaining plate 20 is apparent, which is also referred to as "bumper". A PEG hose 22 is firmly connected to it. The PEG hose 22 has an inner end portion 24 and an outer end portion 26. The inner end portion 24 is firmly connected to the inner retaining plate 20 and has an inner opening 28. From that, a substance can be introduced into a stomach (not shown, see U.S. Pat. No. 4,666,433 A, FIG. 3), e.g. for feeding or treatment with medicaments. A hose according to the prior art is used as a PEG hose 22. It is preferably as transparent as glass, flexible, and has a free internal cross section of 2 to 5 mm; the cross section is round.

Furthermore, the PEG tube comprises an outer retaining plate 30. The PEG hose 22 is routed through that. It is fixed in the outer retaining plate 30; in this case, it may be positioned at any location by means of a clamping device of the outer retaining plate 30. This is the prior art. In this manner, the distance between the inner retaining plate 20 and the outer retaining plate 30 can be adjusted to the respective patient.

Finally, the PEG tube has a funnel adapter 32 at the outer end portion 26. In the exemplary embodiment shown, it is connected to the outer end portion 26 by means of a compression fitting. The funnel adapter 32 shown is the prior art. It comprises a sealing cap.

A valve 34 is located in the PEG hose 22; it is disposed between the outer retaining plate 30 and the outer end portion 26. In this case, a piece of the PEG hose 22 is located on both sides of the valve 34. The valve 34 is connected on each of both sides to the adjacent piece of PEG hose 22, for example by means of a compression fitting as it is used for the funnel adapter 32.

The valve 34 has a two-part valve housing 36, i.e. a first section 38 and a second section 40. Furthermore, it comprises a handling means 42, which is configured as a circular disk with an operating slot 44 in the exemplary embodiment shown. It is located between the two sections 38, 40.

FIG. 2 shows in a sectional view a valve 34 as it can be used in the PEG tube according to FIG. 1. In turn, the valve 34 has a two-part valve housing 36 with a first section 38 and a second section 40, which are tightly connected in the state shown; they are mechanically connected to each other. This is done by suitable means as they are known from the prior art, for example by means of a plugging or latching connection. Each section 38, 40 has on its outer side a conical region; there, the PEG hose 22 can be pushed on. It is retained by means of suitable devices as they are formed, for example, on the funnel adapter 32. In particular, this is done by means of a union nut 41.

Between them, the two sections 38, 40 define a spherical cavity filled by a valve body 46 in the shape of a sphere with a diametral bore 48. This valve body 46 is connected to a short cylindrical portion that extends radially and is part of a handling means 42, which furthermore has a disk that is located outside the two sections 38, 40 and in which an operating slot 44 is provided. The valve 34 according to FIG. 2 is shown in the blocking state. It can be seen that the diameter of the bore 48 corresponds to the diameter of passages in the two sections 38, 40. If the valve body 46 is pivoted by 90° about an axis situated in the paper plane by means of the handling means 42, a continuous channel with a constant cross section is formed.

The valve according to FIG. 2 can be cleaned by separating the two sections 38, 40 from each other. Then, the valve body 46, together with the handling means 42 connected therewith, is free; it can be cleaned just like the sections 38, 40.

In the third exemplary embodiment according to the FIGS. 3 to 6, and also in the fourth exemplary embodiment according to FIG. 7, the PEG hose 22 is located on only one side, namely the left side of the valve 34 in the drawing. One coupling portion 50, respectively, is provided on the other side of the valve 34. It cooperates with a coupling counterpart 52 formed on the funnel adapter 32. In the third exemplary embodiment, the funnel adapter forms a sleeve which reaches over the cylindrical outer shell of the valve 34 in the plugged-together state of the valve 34 and the funnel adapter 32. A collar 56 is provided which radially protrudes all around from the outer shell and is located in the vicinity of a free front edge of the sleeve 54 if the valve 34 and the funnel adapter 32 are plugged together. A collar can be omitted. Particularly if the sleeve 54 is made to be so long in its free inner space that it reaches over the valve housing 36 in its entirety.

In turn, the valve body 46 is formed by a sphere. Similar to the second exemplary embodiment according to FIG. 2, it is connected to a handling means 42.

In the third and fourth exemplary embodiments, the handling means 42 is configure of two parts. A first part 58 of the handling means 42 is permanently connected to the valve body 46, just as in the second exemplary embodiment. This first part 58 is sufficient for operating the valve body 46 if one has a suitable tool. This suitable tool is formed by a second part 60 of the handling means 42. In principle, however, the valve 34 could also already be operated without this second part. The intention is that the first part has an operating slot 44 or a depression, a projection or a hole pattern, i.e. an key arrangement for operation, whereby it is necessary that the first part 58 can be moved only by means of a matching, special tool. In no case should the first part 58 be operable only by means of the fingers. The key arrangement, and also the effort, required for operating the valve body 46 are set such that a patient is not able to operate the valve 34 with means normally available to him.

The valve 34 can be operated manually and without any other tools if the second part 60 cooperates with the first part 58. This takes place when, in the third exemplary embodiment, the funnel adapter 32 and the valve 34 are pushed together in the direction of the arrow 62 up to the stop. The second part 60 is rotatably mounted in the sleeve 54. It is rotatable about a radial axis. It forms a tool on its lower edge, e.g. a rib 64, which can also be described as a blade. The narrow rib 64 protrudes into the free cavity of the sleeve 54, as can also be seen in FIG. 6.

During the plugging process in the direction of the arrow 62, the rib 64 ends up in a furrow 66 in the valve body 46 and then in the operating slot 44 of the first part 58. In the fully plugged-together state, it is no longer situated in the furrow 66, but only in the operating slot 44. If the second part 60 is now rotated, the first part 58 also rotates with it, and accordingly, also the valve body 46.

In the position shown in the FIGS. 3 and 5, the valve body 46 is in the closing state; the passage through the valve housing 36 is fully blocked. In this state, it is possible to pull off the funnel adapter 32 from the valve 34 in the direction opposite to the arrow 62. In any other rotational position, even in an intermediate position, this is not possible.

If a patient twists the first part 58 or the second part 60 starting from the above-mentioned position, it is not possible to plug them together in the direction of the arrow 62. This is possible only when the two parts 58, 60 are in the state in which they are shown in the FIGS. 3 to 6.

FIGS. 4 and 6 show a grip of the second part 60 orientated in the axial direction. This grip should better be disposed twisted by 90° about the rotary axis of the second part 60 in order to directly show the state of the valve body 46. In the transverse position of this grip, the valve is closed. In the longitudinal position, as shown in FIG. 4, but in contrast to this Figure, the valve 34 is opened.

Other configurations are possible. For example, a tool in the shape of a polygon can replace the rib 64, which protrudes in a pin-shaped manner. The furrow 66 can be configured in a rising manner, so that the polygon is lifted and arrives on the top side of the first part 58. When the process of pushing together is continued, it then drops into a recess that corresponds to the polygon and replaces the operating slot 44. The second part 60 has to be pulled up during detachment.

Finally, FIG. 7 shows an exemplary embodiment in which the plugging process of the funnel adapter 32 and the valve 34 and the joining of the first part 58 and the second part 60 of the handling means 42 do not take place simultaneously and are independent of one another. The second part 60 is now disposed on a flexible tab 68 that is firmly connected to the funnel adapter 32. The second part 60 is attached to the free end of the tab. It has a gripping portion and, on the other side of the tab, a tool that corresponds to the rib 64, for example in the shape of a tool or key in an arbitrary form. A fitting recess 70 replacing the operating slot 44 is provided in the first part 58. The tool is pushed into the recess 70; then, the valve body 46 can be operated by means of the gripping portion.

The PEG tube comprises a PEG hose 22, an outer retaining plate 30 through which the PEG hose 22 is routed and in which it is fixed, and a funnel adapter 32 associated with the outer end portion 26 of the PEG hose 22. A tightly sealing valve 34 is disposed either in the PEG hose 22 between the outer retaining plate 30 and the outer end portion 26 or at the outer end portion 26 of the PEG hose 22. In a closing position, the valve 34 blocks the flow-through through the PEG hose 22, and in an opening position unblocks it at least over the full cross section of the PEG hose 22. The valve 34 comprises a valve body 46 and a valve housing 36. The valve body 46 is connected to a handling means 42 accessible from the outside and is movable; it is mounted in the valve housing 36. Preferably, the handling means 42 comprises an operating slot or a corresponding projection or a corresponding depression that permit an operation by means of a matching separate tool, but not by means of human fingers or a simple accessory.

The invention claimed is:

1. A PEG tube comprising:
   an inner retaining plate,
   a PEG hose having an inner end portion and an outer end portion, the inner end portion being firmly connected to the inner retaining plate and defining an inner opening of the PEG hose,
   an outer retaining plate through which the PEG hose is routed and in which it is fixed,
   a funnel adapter located at the outer end portion, and
   a tightly sealing valve disposed at the outer end portion of the PEG hose, wherein the valve blocks flow through the PEG hose in a closed position, partially unblocks flow in an intermediate position, and unblocks flow at least over a full cross section of the PEG hose in an open position, wherein the valve comprises a valve body and a valve housing, the valve body is connected to a handling part accessible from outside the valve housing and is mounted in the valve housing in a configuration in which the valve body is movable between a first position defining the closed position of the valve and a second position defining the open position of the valve, wherein the handling part includes a first part of the handling part permanently disposed on the valve body and a second part of the handling part disposed on the funnel adapter separately from the valve that, when the valve and the funnel adapter are fitted together, automatically engages the first part of the handling part, wherein the second part of the handling part comprises a tool engageable with a mating tool of the first part of the handling part, wherein the PEG hose is located only on an inner side of the valve, the valve is connected on the inner side to the outer end portion of the PEG hose and the valve has at an outer side thereof a coupling portion, the funnel adapter has a coupling counterpart adapted to matingly engage with the coupling portion, and the coupling portion and the coupling counterpart are tightly connectable to and detachable from each other.

2. The PEG tube according to claim 1, wherein the tool of the second part of the handling part is connected to the mating tool of the first part of the handling part.

3. The PEG tube according to claim 2, wherein the valve housing comprises two sections adapted to be connected to each other in a detachable manner.

4. The PEG tube according to claim 3, wherein the valve body is located between the two sections of the valve housing, the valve body is retained in the valve housing when the two sections of the valve housing are connected, and the valve body is removable from the valve housing when the two sections of the valve housing are separated from one another.

5. The PEG tube according to claim 2, wherein the valve body is spherical, conical, cylindrical or disk-shaped.

6. The PEG tube according to claim 2, wherein the second part of the handling part is rigidly connected to the funnel adapter.

7. The PEG tube according to claim 2, wherein the second part of the handling part is flexibly connected to the funnel adapter.

8. The PEG tube according to claim 2, wherein the valve comprises a groove or a rib adapted to receive and guide the tool of the second part of the handling part when the funnel adapter and the valve are fitted together.

9. The PEG tube according to claim 1, wherein the valve housing comprises two sections adapted to be connected to each other in a detachable manner.

10. The PEG tube according to claim 9, wherein the valve body is located between the two sections of the valve housing the valve body is retained in the valve housing when the two sections of the valve housing are connected, and the valve body is removable from the valve housing when the two sections of the valve housing are separated from one another.

11. The PEG tube according to claim 10, wherein the valve body is spherical, conical, cylindrical or disk-shaped.

12. The PEG tube according to claim 10, wherein the second part of the handling part is rigidly connected to the funnel adapter.

13. The PEG tube according to claim 9, wherein the valve body is spherical, conical, cylindrical or disk-shaped.

14. The PEG tube according to claim 9, wherein the second part of the handling part is rigidly connected to the funnel adapter.

15. The PEG tube according to claim 9, wherein the second part of the handling part is flexibly connected to the funnel adapter.

16. The PEG tube according to claim 9, wherein the valve comprises a groove or a rib adapted to receive and guide the tool of the second part of the handling part when the funnel adapter and the valve are fitted together.

17. The PEG tube according to claim 1, wherein the valve body is spherical, conical, cylindrical or disk-shaped.

18. The PEG tube according to claim 1, wherein the second part of the handling part is rigidly connected to the funnel adapter.

19. The PEG tube according to claim 1, wherein the second part of the handling part is flexibly connected to the funnel adapter.

20. The PEG tube according to claim 1, wherein the valve comprises a groove or a rib adapted to receive and guide the tool of the second part of the handling part when the funnel adapter and the valve are fitted together.

* * * * *